US008925557B2

(12) United States Patent
Liao

(10) Patent No.: US 8,925,557 B2
(45) Date of Patent: Jan. 6, 2015

(54) GEL NAIL STICKER AND MANUFACTURING PROCESS THEREOF

(76) Inventor: Jingyi Liao, Guangzhou (CN)

( * ) Notice: Subject to any disclaimer, the term of this patent is extended or adjusted under 35 U.S.C. 154(b) by 0 days.

(21) Appl. No.: 13/498,527

(22) PCT Filed: Aug. 2, 2011

(86) PCT No.: PCT/CN2011/077902
§ 371 (c)(1),
(2), (4) Date: Mar. 27, 2012

(87) PCT Pub. No.: WO2013/000189
PCT Pub. Date: Jan. 3, 2013

(65) Prior Publication Data
US 2014/0150812 A1 Jun. 5, 2014

(30) Foreign Application Priority Data
Jun. 28, 2011 (CN) .......................... 2011 1 0180451

(51) Int. Cl.
*A45D 24/00* (2006.01)
*A45D 7/00* (2006.01)
*A45D 29/00* (2006.01)
*A61K 9/00* (2006.01)
*A61K 8/00* (2006.01)
*A61K 8/18* (2006.01)
*A61Q 3/00* (2006.01)
*A45D 31/00* (2006.01)
*B41M 1/12* (2006.01)

(52) U.S. Cl.
CPC .............. *A45D 29/001* (2013.01); *A45D 31/00* (2013.01); *B41M 1/12* (2013.01); *A45D 2029/005* (2013.01)
USPC ................ 132/200; 132/73; 424/401; 424/61

(58) Field of Classification Search
CPC ................ A45D 31/00; A45D 29/001; A45D 2029/005; B41M 1/40; B41M 1/12; A61Q 3/02
USPC ............ 132/73, 200, 285, 319, 333; 101/129, 101/483, 35; 40/638; 428/403, 40.1, 42.1, 428/67, 41.7, 41.8; 424/401, 61
See application file for complete search history.

(56) References Cited

U.S. PATENT DOCUMENTS 4,824,702 A * 4/1989 Straub ............................ 428/15
5,262,224 A * 11/1993 Ozaki et al. ................ 428/195.1

(Continued)

FOREIGN PATENT DOCUMENTS

| | | |
|---|---|---|
| KR | 20100119132 | 11/2010 |
| KR | 20100125837 | 12/2010 |
| WO | WO 95/02344 | 1/1995 |

*Primary Examiner* — Vanitha Elgart
(74) *Attorney, Agent, or Firm* — Diederiks & Whitelaw, PLC

(57) ABSTRACT

A gel nail sticker includes a base film layer, and a pressure-sensitive adhesive layer, wherein the base film layer is a PET release film or release paper, and the pressure-sensitive adhesive layer is bonded to the bottom of a soft layer and connected with the base film layer; the soft layer is printed with at least one layer of screen printing color layer or shimmering powder layer by screen printing; a first crystal gel layer covers on the surface of the shimmering powder layer or the screen printing color layer, and a second crystal gel layer envelops the first crystal gel layer, the shimmering powder layer and the screen printing color layer, and is bonded to the soft layer and the pressure-sensitive adhesive layer. A manufacturing process for the gel nail sticker, includes screen printing of the various layers.

1 Claim, 2 Drawing Sheets

(56) References Cited

U.S. PATENT DOCUMENTS

| | | | | |
|---|---|---|---|---|
| 7,622,175 | B2 * | 11/2009 | Pallotta et al. | 428/40.1 |
| 7,709,070 | B2 * | 5/2010 | Kinsey et al. | 428/40.1 |
| 8,586,164 | B2 * | 11/2013 | Weber et al. | 428/40.1 |
| 2003/0157287 | A1 * | 8/2003 | Song | 428/40.1 |
| 2004/0161568 | A1 * | 8/2004 | Truog et al. | 428/40.1 |
| 2005/0022834 | A1 * | 2/2005 | Hwang | 132/73 |
| 2005/0150508 | A1 * | 7/2005 | Downs et al. | 132/73 |
| 2005/0217686 | A1 * | 10/2005 | Lee | 132/200 |
| 2005/0236100 | A1 * | 10/2005 | Arisawa | 156/290 |
| 2006/0037624 | A1 * | 2/2006 | Ilekti | 132/73 |
| 2006/0204702 | A1 | 9/2006 | Thevenet | |
| 2007/0025936 | A1 * | 2/2007 | Park | 424/61 |
| 2008/0087291 | A1 * | 4/2008 | Jordan | 132/200 |
| 2010/0212681 | A1 * | 8/2010 | Park | 132/200 |
| 2011/0117174 | A1 * | 5/2011 | Kergosien et al. | 424/443 |
| 2012/0263905 | A1 * | 10/2012 | Park | 428/41.8 |
| 2013/0017352 | A1 * | 1/2013 | Chang | 428/41.8 |
| 2013/0032163 | A1 * | 2/2013 | Roescheisen | 132/200 |
| 2013/0059104 | A1 * | 3/2013 | Chang | 428/41.8 |
| 2013/0139839 | A1 * | 6/2013 | Chang | 132/200 |
| 2013/0199559 | A1 * | 8/2013 | Haile | 132/200 |
| 2013/0220355 | A1 * | 8/2013 | Park | 132/73 |
| 2013/0319441 | A1 * | 12/2013 | Ma | 132/200 |
| 2013/0319444 | A1 * | 12/2013 | Pak | 132/200 |

* cited by examiner

GEL NAIL STICKER AND MANUFACTURING PROCESS THEREOF

CROSS-REFERENCE TO RELATED APPLICATIONS

This application represents a National Stage application of PCT/CN2011/077902 entitled "Gel Nail Sticker and Manufacturing Process Thereof" filed Aug. 2, 2011, pending.

FIELD OF THE INVENTION

The present invention relates to beauty decoration products, and in particular to nail stickers for decorating female fingers and toes and the manufacturing process thereof.

BACKGROUND OF THE INVENTION

Chinese patent no. ZL 03260146.8 discloses a stick type nail sticker. This kind of nail sticker has following disadvantages. First of all, to change the shape of pattern each time, it is necessary to change the mould, which involves high costs and takes a long time. Secondly, if the gap between patterns is less than 2 mm, it can not be realized by the mould. Thirdly, it uses the self adhesive to be attached to the nails, which results in a short lifetime when used repeatedly. Finally, the pattern is sprayed onto a resin film, and thus the obtained pattern is in lack of stereovision and fineness.

SUMMARY OF THE INVENTION

To overcome the disadvantages of the prior art, a gel nail sticker and the manufacturing process thereof are provided. It has a long lifetime, and its patterns are rich and varied, with good stereovision and fineness. It is also easy to produce the gel nail sticker of the invention which is more beautiful and with aesthetic effect of gel. The manufacturing process for the nail sticker of the invention is simple, and the screen printing is used so as to allow the products to have a good stereovision and a high fineness.

To Achieve the Above Object of the Present Invention:

A gel nail sticker comprises a base film layer, a pressure-sensitive adhesive layer, wherein the base film layer is a PET release film or release paper, and the pressure-sensitive adhesive layer is bonded to the bottom of a soft layer and connected with the base film layer. The soft layer is printed with at least one of a screen printing color layer or a shimmering powder layer by screen printing. A first crystal gel layer covers on the surface of the shimmering powder layer or the screen printing color layer. A second crystal gel layer envelops the first crystal gel layer, the shimmering powder layer and the screen printing color layer, and is bonded to the soft layer and the pressure-sensitive adhesive layer.

Preferably, the shimmering powder layer is a layer of one or more materials selected from a group consisting of glitter powder, flashing powder, laser powder, camouflage powder, iridescence pigment and pearl powder, or a layer of tinsel or electrochemical aluminium layer.

Preferably, the shimmering powder layer is printed on the soft layer by screen printing. At least one screen printing color layer is printed on the shimmering powder layer by screen printing. The first crystal gel layer covers on the top of the screen printing color layer, and the crystal gel layer envelops the first crystal gel layer, the Shimmering powder layer and the screen printing color layer, and is bonded to the soft layer and the pressure-sensitive adhesive layer.

Preferably, the at least one screen printing color layer is printed on the soft layer by screen printing, and the shimmering powder layer is printed on the top of the screen printing color layer by screen printing, and the first crystal gel layer covers on the shimmering powder layer.

Furthermore, a manufacturing process for the gel nail sticker is provided. The manufacturing process comprises:

a. screen printing of a pressure-sensitive adhesive layer: select a PET release film or release paper as a base film layer which has a thickness of 0.05-0.1 mm; a pressure-sensitive adhesive layer is printed on the base film layer by screen printing, and dried for 20-50 minutes at room temperature of 25-35° C.;

b. screen printing of a soft layer: the soft layer is a mixture of isophorone and Ethylene glycol monobutyl ether, with a weight ratio of 40:60. The soft layer is printed on the pressure-sensitive adhesive layer by screen printing to isolate the pressure-sensitive adhesive layer from ink, and then dried for 80-120 minutes at room temperature of 25-35° C.;

c. screen printing of a screen printing color layer: the color layer is an ink layer; according to the requirement of patterns, if the pattern is in one color, then only one ink layer is printed, and if the pattern is in two colors, two layers are printed, and so forth, by screen overprinting, in order to ensure saturation of the ink; every color is printed twice by screen printing, and dried instantly at room temperature of 25-35° C.;

d. screen printing of a shimmering powder layer: the shimmering powder layer is a layer of various models of glitter powder, flashing powder, laser powder, camouflage powder, iridescence pigment and pearl powder, or a layer of tinsel or electrochemical aluminium layer, and according to the purpose of design, the shimmering powder layer can be printed under or above the ink layer twice by screen printing, and dried for 20-50 minutes at room temperature of 25-35° C., to increase decoration of products;

e. screen printing of a crystal gel layer: a first crystal gel layer and a second crystal gel layer are layers of epoxide resin glue; at room temperature of 25-35° C., epoxide resin glue is printed once by screen printing, and after waiting for 10-15 minutes, the first crystal gel layer (6) is formed, and then print epoxide resin glue is printed by screen printing for the second time, and after waiting for 160-200 minutes, allowing the epoxide resin glue to flow naturally to form the second crystal gel layer which is transparent and arc-shaped, and higher in the middle and lower on both sides.

Advantages of the Invention

1. The present invention uses the screen printing to print the pattern with the shimmering powder, which overcomes the problems in the spray painting in prior art, and avoids die sinking and can print the patterns with a gap less than 2 mm between each other and with good stereovision and high fineness.

2. The outside of the gel nail sticker of the present invention is composed of crystal epoxide resin gel. The crystal epoxide resin gel flows to be flat naturally to form a smoothly transparent arc-shaped layer which is higher in the middle and lower on both sides. The gel nail sticker obtained in the present invention is high grade, with a strong sense of streamline, and is transparent like crystal, with various colors and shimmering powder allowing the product to be very beautiful.

Figure 1:
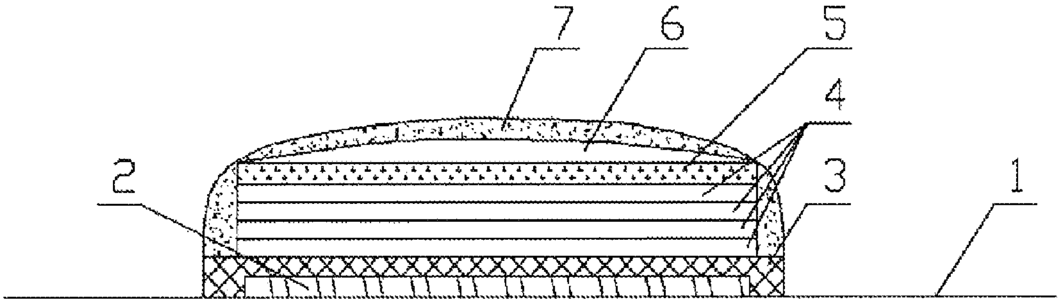
FIG. 1 shows a schematic view of the structure according to the embodiment 1.

In the figures: 1. the base film layer; 2. the pressure-sensitive adhesive layer; 3. the soft layer; 4. the screen printing color layer; 5. the shimmering powder layer; 6. the first crystal gel layer; 7. the second crystal gel layer.

DETAILED DESCRIPTION OF THE PREFERRED EMBODIMENT

Embodiment 1

The shimmering powder layer 5 is a layer of one or more materials selected from a group consisting of glitter powder, flashing powder, laser powder, camouflage powder, iridescence pigment and pearl powder, or a layer of tinsel or electrochemical aluminium layer.

The soft layer 3 is a mixture of isophorone and Ethylene glycol monobutyl ether, with a weight ratio of 40:60. The soft layer 3 is on the surface of the pressure-sensitive adhesive layer 2, to isolate the pressure-sensitive adhesive layer 2 from ink of the screen printing color layer 4.

The first crystal gel layer 6 and the second crystal gel layer 7 are both obtained by solidifying transparent epoxide resin gel.

As shown in FIG. 1, a gel nail sticker comprises a base film layer 1, and a pressure-sensitive adhesive layer 2, wherein the base film layer 1 is a PET release film or release paper, and the pressure-sensitive adhesive layer 2 is bonded to the bottom of a soft layer 3 and connected with the base film layer. The soft layer 3 has at least one screen printing color layer 4 or at least one shimmering powder layer 5 by screen printing. A first crystal gel layer 6 covers on the surface of the shimmering powder layer 5 or the screen printing color layer 4, and a second crystal gel layer 7 envelops the first crystal gel layer 6, the shimmering powder layer 5 and the screen printing color layer 4, and bonded to the soft layer 3.

The shimmering powder layer 5 is a layer of one or more materials selected from a group consisting of glitter powder, flashing powder, laser powder, camouflage powder, iridescence pigment and pearl powder, or a layer of tinsel or electrochemical aluminium layer.

The shimmering powder layer 5 is printed by screen printing. At least one screen printing color layer 4 is printed on the shimmering powder layer 5 by screen printing. The first crystal gel layer 6 covers on the top of the screen printing color layer 4.

A manufacturing process for the gel nail sticker comprises, a. screen printing of the pressure-sensitive adhesive layer: select the PET release film or release paper as the base film layer 1 which has a thickness of 0.05-0.1 mm; a pressure-sensitive adhesive layer 2 is printed on the top of the base film layer 1 by screen printing, and dried for 20-50 minutes at room temperature of 25-35° C.;

b. screen printing of the soft layer: the soft layer 3 is a mixture of isophorone and Ethylene glycol monobutyl ether, with a weight ratio of 40:60. The soft layer 3 is printed on the pressure-sensitive adhesive layer 2 by screen printing to isolate the pressure-sensitive adhesive layer from ink, and then dried for 80-120 minutes at room temperature of 25~35° C.;

c. screen printing of the screen printing color layer: the color layer 4 is an ink layer; according to the requirement of patterns, if the pattern is in one color, then only one ink layer is printed, and if the pattern is in two colors, two layers are printed, and so forth, and in order to ensure saturation of the ink, every color is printed twice by screen printing, and dried instantly at room temperature of 25-35° C.;

d. screen printing of the shimmering powder layer: the shimmering powder layer 5 is a layer of various models of glitter powder, flashing powder, laser powder, camouflage powder, iridescence pigment and pearl powder, or a layer of tinsel or electrochemical aluminium layer, and according to the purpose of design, the shimmering powder layer can be printed under or above the ink layer twice by screen printing, and dried for 20-50 minutes at room temperature of 25-35° C., to increase decoration of products;

e. screen printing of the crystal gel layer: a first crystal gel layer 6 and a second crystal gel layer 7 are layers of epoxide resin glue; at room temperature of 25-35° C., print epoxide resin glue is printed once by screen printing, and after waiting for 10-15 minutes, the first crystal gel layer 6 is formed, and then print epoxide resin glue is printed by screen printing for the second time, and after waiting for 160-200 minutes, allowing the epoxide resin glue to flow naturally to form the second crystal gel layer 7 which is transparent and arc-shaped, and higher in the middle and lower on both sides.

Embodiment 2

Figure 2:
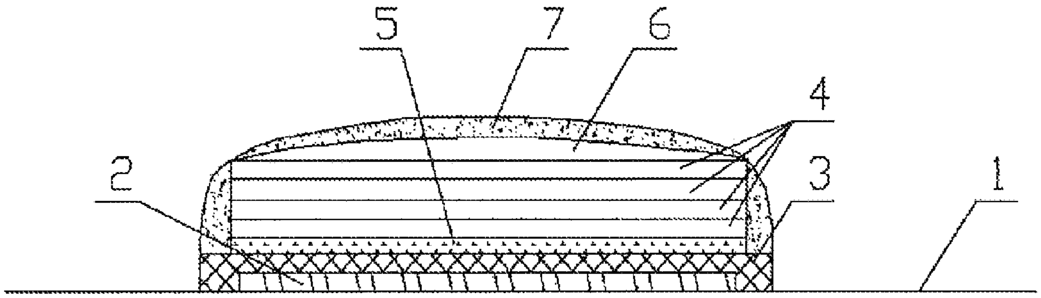
FIG. 2 shows a schematic view of the structure according to the embodiment 2.

As shown in FIG. 2, four screen printing color layers 4 are printed on the soft layer 3 by screen printing, and the shimmering powder layer 5 is printed on the top of the four screen printing color layers 4 by screen printing, and the first crystal gel layer 6 covers on the shimmering powder 5. The rest is the same with the embodiment 1.

Figure 3:
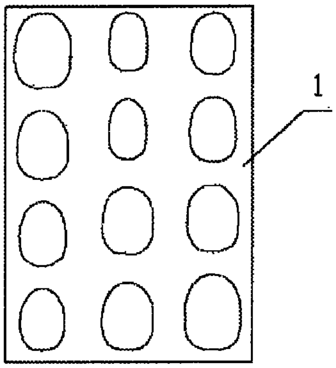
FIG. 3 shows a schematic view of the structure of a plurality of the products sold in sets according to present invention.
Figure 4:
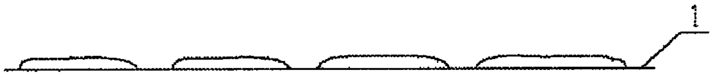
FIG. 4 shows a right view of FIG. 3.

Introduction for Use:

As shown in FIGS. 3 and 4, when the gel nail sticker is sold, a plurality of gel nail stickers are arranged on the same piece of the base film layer 1 (the arrangements are not limited to that shown in the attached figures). One gel nail sticker can be taken from the base film layer 1, and bonded to human's fingers or toes for beautification by the pressure-sensitive adhesive layer 2. When in use, the nails are cleaned first, then a nail sticker with a suitable dimension is selected, and then the nail sticker is lightly taken from the base film layer by using tweezers or nails. The nail sticker is bonded in the middle of the nail. Preferably, the nail sticker is bonded to the nail once. Obviously, the nail sticker can be bonded repeatedly. When removing the gel nail sticker, the nail sticker is torn slightly from the edge of the pattern.

Operation Principle: the most important feature of the present invention is to print the pattern required on the layers from the bottom to the top, which respectively are the pressure-sensitive adhesive layer 2, the soft layer 3, the color layer 4 and the shimmering powder layer 5, and the above layers are then combined with the first crystal gel layer 6 and the second crystal gel layer 7. The cutting die is not necessary, while the pattern is good in stereovision and high in fineness.

The first crystal gel layer 6 and the second crystal gel layer 7 flow to be flat naturally. They are transparent arc-shaped layers which are higher in the middle and lower on both sides. The gel nail sticker of the present invention is high in grade, with a strong sense of streamline, and is transparent like crystal, with various colors and shimmering powder, allowing the product to be very beautiful.

What is claimed is:

1. A manufacturing process for a gel nail sticker, comprising, a. screen printing of a pressure-sensitive adhesive layer, wherein a PET release film or release paper is selected as a base film layer having a thickness of 0.05-0.1 mm and the pressure-sensitive adhesive layer is printed on a top of the base film layer by screen printing, and dried for 20-50 minutes at room temperature of 25-35° C.;

b. screen printing of a soft layer, wherein the soft layer is a mixture of isophorone and Ethylene glycol monobutyl ether, with a weight ratio of 40:60, the soft layer is printed on the pressure-sensitive adhesive layer by screen printing to isolate the pressure-sensitive adhesive layer from ink, and then the soft layer is dried for 80-120 minutes at room temperature of 25-35° C.;

c. screen printing of one or more screen printing color layers on said soft layer, wherein each color layer is an ink layer, with the number of ink layers being equal to the number of colors in a pattern for the gel nail sticker, and each color layer being printed by screen overprinting while, in order to ensure saturation of the ink, every color is printed twice by screen printing, and instantly dried at room temperature of 25-35° C.;

d. screen printing of a shimmering powder layer, wherein the shimmering powder layer is a layer of various models of glitter powder, flashing powder, laser powder, camouflage powder, iridescence pigment and pearl powder, or a layer of tinsel or an electrochemical aluminium layer, and, for design purposes, the shimmering powder layer being printed under or above the one or more screen printing color layers twice by screen printing, and dried for 20-50 minutes at room temperature of 25-35° C., to increase a level of decoration;

e. screen printing of a crystal gel layer including a first crystal gel layer and a second crystal gel layer of epoxide resin glue wherein, at room temperature of 25-35° C., epoxide resin glue is printed once by screen printing, and after waiting for 10-15 minutes, the first crystal gel layer is formed, and then epoxide resin glue is printed by screen printing for a second time, with the epoxide resin glue being given 160-200 minutes to flow naturally to form the second crystal gel layer which is transparent and arc-shaped, and higher in the middle but lower on both sides, said first crystal gel layer covering said one or more screen printing color layers or said shimmering powder layer and said second crystal gel layer enveloping said first crystal gel layer, said shimmering powder layer, and said one or more screen printing color layers.

* * * * *